(12) United States Patent
Helland

(10) Patent No.: US 7,212,870 B1
(45) Date of Patent: May 1, 2007

(54) DUAL HELIX ACTIVE FIXATION STIMULATION LEAD

(75) Inventor: John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 195 days.

(21) Appl. No.: 10/944,292

(22) Filed: Sep. 16, 2004

(51) Int. Cl.
*A61N 1/04* (2006.01)

(52) U.S. Cl. .................... 607/127; 607/126; 607/122

(58) Field of Classification Search ............... 607/127, 607/126, 122
See application file for complete search history.

(56) References Cited

U.S. PATENT DOCUMENTS

| | | | | |
|---|---|---|---|---|
| 3,750,650 A | * | 8/1973 | Ruttgers | 600/376 |
| 4,010,758 A | | 3/1977 | Rockland et al. | 128/418 |
| 4,355,642 A | * | 10/1982 | Alferness | 600/374 |
| 5,328,442 A | * | 7/1994 | Levine | 600/17 |
| 5,545,201 A | | 8/1996 | Helland et al. | 607/127 |
| 5,755,764 A | * | 5/1998 | Schroeppel | 607/122 |
| 6,085,119 A | * | 7/2000 | Scheiner et al. | 607/122 |
| 6,397,109 B1 | | 5/2002 | Cammilli et al. | 607/123 |
| 6,937,897 B2 | * | 8/2005 | Min et al. | 607/9 |
| 2002/0103521 A1 | | 8/2002 | Swoyer et al. | 607/116 |
| 2003/0073972 A1 | * | 4/2003 | Rosenman et al. | 604/502 |

* cited by examiner

*Primary Examiner*—Robert Pezzuto
*Assistant Examiner*—Shevon Johnson

(57) ABSTRACT

An implantable lead for use with an implantable medical device includes a lead body with first and second electrical conductors extending between its proximal and distal ends. An electrical connector at the proximal end of the lead body includes terminals electrically connected to the first and second conductors. First and second coaxial active fixation helices are coupled to the lead body's distal end, one being an anode, the other an electrically isolated cathode. Each helix has an outer peripheral surface with alternating insulated and un-insulated portions along its length with about a half of the surface area being insulated. The un-insulated portions of the helices may be formed as a plurality of islands in the insulated portions, or as rings spaced by insulative rings, or as longitudinally extending strips spaced by longitudinally extending insulative strips.

27 Claims, 8 Drawing Sheets

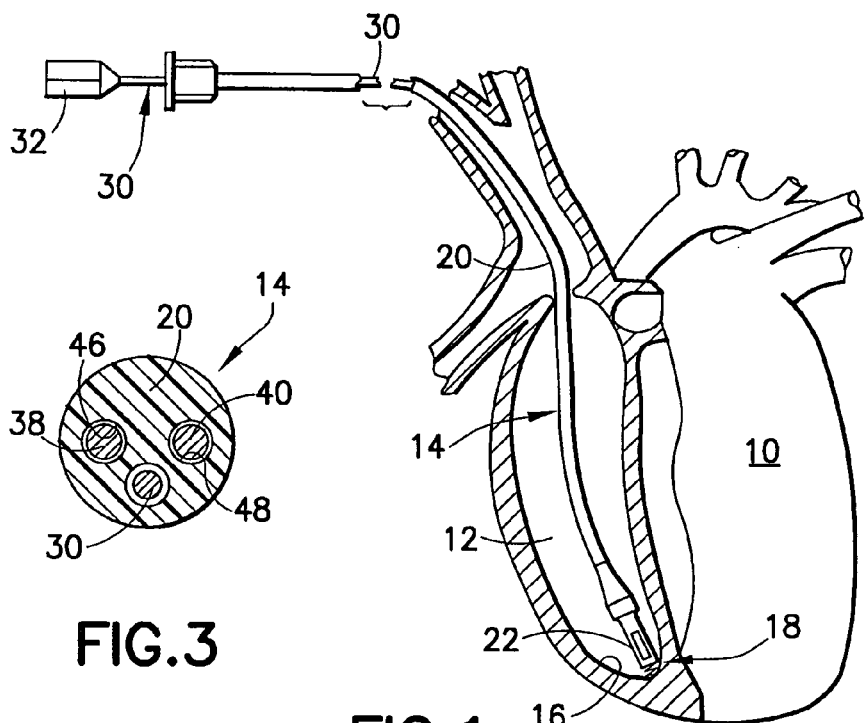
FIG.3
FIG.1
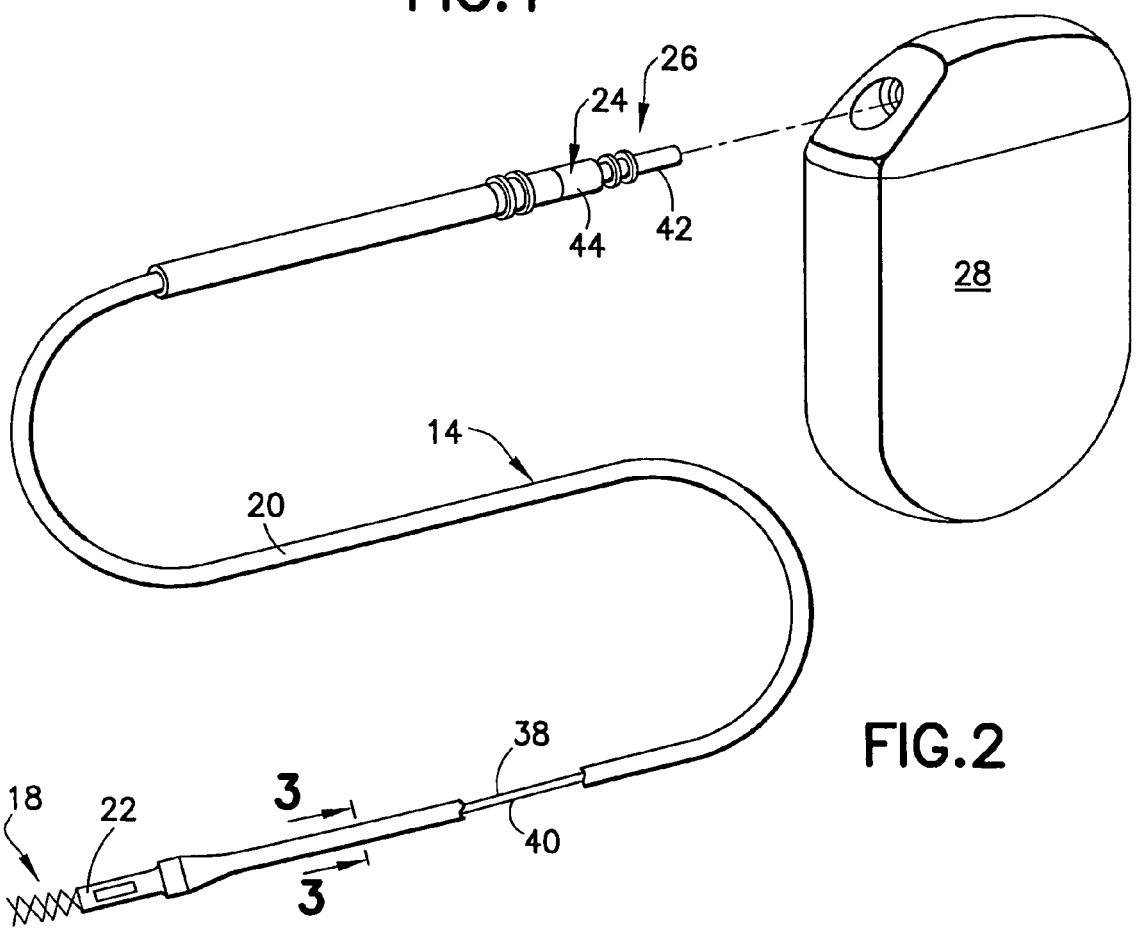
FIG.2

DUAL HELIX ACTIVE FIXATION STIMULATION LEAD

FIELD OF THE INVENTION

The present invention relates generally to implantable leads for medical devices which provide stimulating pulses to selected body tissue, for example, the heart, and more particularly, to an implantable stimulation lead having a bipolar active fixation electrode for pacing and sensing electrical activity in the heart.

BACKGROUND OF THE INVENTION

Pacing leads having at least two electrodes adjacent to the distal end are used for bipolar pacing, as well as for providing sensory information to an attached cardiac pacemaker. Generally, bipolar pacing leads are either active or passive fixation, the former using tines typically, and the latter using a screw mechanism. A bipolar active fixation lead can have its helical screw be one of its electrodes and a ring electrode spaced from the distal end of the pacing lead as its second electrode. The spacing between the two electrodes is usually dependent upon the physical constraints attendant with the design of the distal end of the lead and its materials. However, it is beneficial to have the two electrodes very close together, particularly for sensing differences in the electrical signals in the heart.

The design and proximity of the electrodes can be such as to enhance the electrical signal sensing capability of the bipolar lead to allow improved discrimination of the sensed signals. Generally, abnormal electrical activity such as ventricular tachycardia or ventricular fibrillation results in electrical signals having differing characteristics. For example, in a given patient, ventricular tachycardia may produce electrical potentials much higher than normal sinus rhythm. By comparison, ventricular fibrillation may produce electrical potentials which are smaller than that of normal sinus rhythm signals. Similarly, in the atrium, electrical potentials also vary whether the signals are normal sinus rhythm signals or due to atrial tachycardia or fibrillation. The ability of a pacing lead to discriminate between the signals is at least partially dependent upon the spacing between the two electrodes. The ability to sense the electrical potential across a small area within the myocardial tissue would be very beneficial in allowing a pacing system to discriminate between the various electrical signals within the heart. In addition, minimizing the spacing between the electrodes used for bipolar sensing would also minimize the sensing of "far field" electrical signals generated elsewhere in the heart or from, for example, nearby skeletal muscles.

Typical of the known prior art is U.S. Pat. No. 4,010,758 to Rockland et al. which discloses a bipolar electrode structure comprising a first, helix-configured electrode adapted to be implanted within the body tissue, for example, the heart, by rotation or screwing and a second, annularly-shaped electrode disposed substantially concentric about the first electrode upon the surface of the tissue, for example, the epicardium.

Another instance of the prior art is found in U.S. Pat. No. 5,545,201 to Helland et al. that discloses an implantable bipolar pacing lead having a bipolar active fixation electrode for use with a cardiac pacemaker. The bipolar active fixation electrode may include a pair of coaxial electrodes, separated by an intermediate insulator, formed into the shape of a helix. The bipolar electrode helix is preferably advanceable from a distal end of the bipolar pacing lead. At the tip of the bipolar electrode helix, the outer electrode is removed, so that the intermediate insulator and the inner electrode extend from the outer electrode, spacing the two electrodes a distance of between 0.1 and 5.0 mm.

U.S. Pat. No. 6,397,109 discloses an implantable lead system that includes a coronary sinus stent supporting multiple electrodes, the stent structure kept in its compressed form while introduced into the access vein, then expanded, dilating a bifurcation of the lead and pushing the electrodes against the cardiac walls. A suitable pre-curvature is imparted to the lead body along its length to enable ease of positioning of the lead structure in the coronary sinus.

It was in light of the foregoing that the present invention was conceived and has now been reduced to practice.

SUMMARY

According to one illustrative embodiment, an implantable lead is described for use with an implantable medical device and includes a lead body with first and second electrical conductors extending between its proximal and distal ends. An electrical connector at the proximal end of the lead body includes terminals electrically connected to the first and second conductors. First and second coaxial active fixation helices are coupled to the lead body's distal end, one being an anode, the other a cathode. Each helix has an outer peripheral surface that is uninsulated in one embodiment or partially insulated to various extents, in other embodiments. Other embodiments utilize insulation that can be alternating insulated and un-insulated portions along its length with about a half of the surface area being insulated. The un-insulated portions of the helices may be formed as a plurality of islands in the insulated portions, or as rings spaced by insulative rings, or as longitudinally extending strips spaced by longitudinally extending insulative strips.

As mentioned above, active fixation bipolar cardiac pacing and/or sensing leads typically utilize a helix for the fixation of the lead's distal tip to endocardial tissue, at various sites either in the right ventricle or in the right atrium. One property of such leads is that they commonly use the helix as an active electrode, usually the cathode, whereas the anode electrode is typically ring shaped, typically positioned 8 to 28 mm proximal to the helix tip electrode. Such leads are very commonly used for right atrial pacing and sensing because they are so effective at remaining secure at the site the implanting physician wants. However, such leads can easily also sense far field R-wave signals or other far-field signals. This can also be true for leads positioned in the RV where they can sense FF P-waves or other FF signals. In an effort to reduce the sensed far field signals, efforts have been undertaken to develop a lead which provides for a tip to ring electrode separation of only about 1.1 mm. Such a design can significantly reduce the size of far field signals.

However, one of the concerns of such a lead is that the anode ring electrode may be positioned in the blood pool and thereby the local sensed P-Wave signal can potentially be attenuated to be too low for the device to effectively use the signals to assist in operating the various algorithms. The local P-wave may also be more prone to morphology, frequency content, and amplitude variation due to the anode ring electrode's variation in its orientation to the atrial endocardium. Thus, a drawback to this current design approach would be that, in some cases, the sensing of the local P-wave may be too extensively compromised or varied to be useful.

What is disclosed, then, is a simple apparatus in which a new lead utilizes all the identical design, material, and processing as current state-of-the-art bipolar active fixation leads, except that the lead has no anode ring electrode. Instead, the helix fixation is actually of a dual helix/dual electrode construction, on the same axis, where one helix is the cathode and the other helix is an anode. With this approach, the anode helix can be a fully active helix bearing no insulation (for example, having about a 2 mm extension, with two turns, using 0.012 in diameter wire, and having a surface area of about 8 sq. mm). At the same time, the cathode helix can be identical in physical size to the anode helix, but a portion of it, specifically, the proximal portion, may be insulated so that the active surface area is about 3 or 4 sq. mm. This helix could also have about half of the surface masked-off in a way such that the entire cathode helix has small sections along its length intermittently insulated and un-insulated, creating a "full" length helix but with only about half the active surface area. Such dimensions and designs assure that the typical pacing impedance should always be at least 500 to 600 ohms or higher. Alternatively, various insulation amounts could be selectively used on either the anode helix or the cathode helix at various locations, so as to tailor the pacing impedance and/or sensing and/or stimulation characteristics to achieve various attributes or meet various requirements. The electrode's active surfaces would also utilize highly electrically efficient coatings such as titanium nitride (TiN). Importantly, this design assures that both electrodes are actually embedded in the myocardium. This feature allows for improved, more uniform sensing and pacing.

Other and further features, advantages, and benefits will become apparent in the following description taken in conjunction with the following drawings. It is to be understood that the foregoing general description and the following detailed description are exemplary and explanatory but are not to be restrictive. The accompanying drawings which are incorporated in and constitute a part of this invention, illustrate certain embodiments. Like numerals refer to like parts throughout the disclosure.

BRIEF DESCRIPTION OF THE DRAWINGS

The foregoing aspects and other features are explained in the following description, taken in connection with the accompanying drawings, wherein:

FIG. 1 is a perspective view illustrating a heart with a portion cut away to reveal an implantable lead assembly, which may embody an illustrative embodiment, secured therein to a wall of the heart;

FIG. 2 is a perspective view of an implantable lead in combination with a stimulating device such as a pacemaker;

FIG. 3 is a cross section view taken generally along line 3—3 in FIG. 2;

DETAILED DESCRIPTION OF THE PREFERRED EMBODIMENTS

Figure 4:
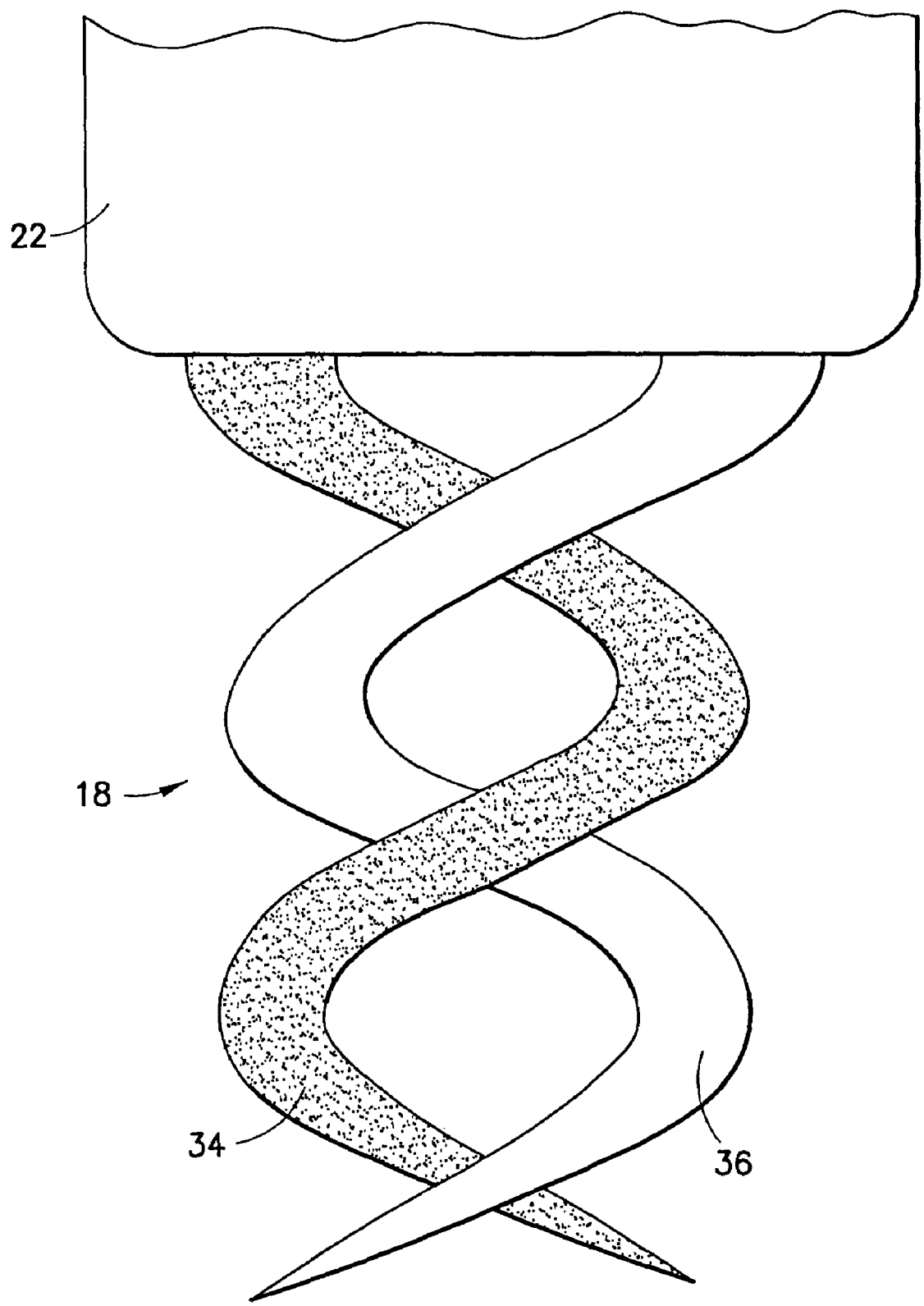
FIG. 4 is a detail elevation view of a distal end of a lead and specifically illustrating an electrode assembly according to one illustrative embodiment.

Referring now to FIG. 1, there is shown a diagrammatic perspective view partially cut away and shown in section of a heart 10 into the right ventricle 12 of which is inserted a body implantable lead 14 of the endocardial type incorporating features of the present invention. Although the present invention will be described with reference to the embodiments shown in the drawings, it should be understood that the present invention can be embodied in many alternate forms or embodiments. In addition, any suitable size, shape or type of elements or materials could be used. The lead 14 of an active fixation design, may be attached to an interior wall 16 of the heart 10 by means of an active fixation helical electrode assembly 18 which is fixated by screwing the helical electrode assembly through the heart's endocardium into the heart's myocardium. It will be understood that such a lead could also be fixated by screwing the helical electrode assembly through the exterior or epicardial surface of the heart into the heart's myocardium.

As further illustrated, the lead 14 also includes an insulating sheath 20 interconnecting the electrode assembly 18 at a distal end 22 of the lead 14, secured to the heart's interior wall 16, and an electrical connector 24 at a proximal end 26 to which can be attached a source of electrical energy such as a pacemaker 28 (FIG. 2). In FIG. 1, a stylet 30 is illustrated inserted within the insulating sheath 20 and may be used with the aid of a proximal manipulating device 32 to provide rigidity to the lead 14 during insertion of the lead into the heart 10. The manipulating device 32 is distant from the distal tip end of the lead and may be a finger grip at a proximal extremity of the stylet 30 provided for controlling the introduction of the stylet into the lead 14 and its subsequent withdrawal.

It was earlier noted that the invention is an improvement over current bipolar active fixation leads, utilizing most of the components of current leads, except that the lead of the invention has no anode ring electrode. Instead, the helix fixation is actually a dual helix/dual electrode assembly, on the same axis, where one helix is the cathode and the other helix is an anode. Thus, viewing especially FIG. 4, the electrode assembly 18 includes first and second active fixation helices 34, 36, respectively, coupled to the distal end of the lead body in a coaxial relationship. The first active fixation helix 34 is an anode and the second active fixation helix 36 is a cathode. In turn, first and second conductors 38 (anode conductor), 40 (cathode conductor) (FIGS. 2 and 3) electrically interconnect each of the active fixation electrodes 34, 36 and first and second terminals 44 (anode terminal), 42 (cathode terminal), respectively, of the electrical connector 24. In FIG. 3, the conductors are seen to be received within lumina 46, 48, respectively, of the insulating sheath 20 which, thereby serves to electrically separate the respective conductors of the active fixation helices 34, 46.

In a known manner, the lead's electrode assembly 18 may be fixated into tissue or retracted from tissue by turning a screwdriver configured stylet (not shown) which turns the lead and its helix electrode assembly 18 about its longitudinal axis. Alternatively, the two helices may be fixedly exposed and the whole lead body rotated manually clockwise to fixate the helices into cardiac tissue (or counterclockwise to unscrew the two helices from cardiac tissue). Still another known approach for helix fixation is to cover the helices with a substance such as Mannital or PEG (polyethyleneglycol), which protects vasculature tissue from the helices' sharp tips during the lead's venous insertion, which dissolves or melts shortly after the lead tip is at the appropriate implant site. Then the exposed helices can then be screwed into the cardiac tissue by rotating the lead body.

Figure 4A:
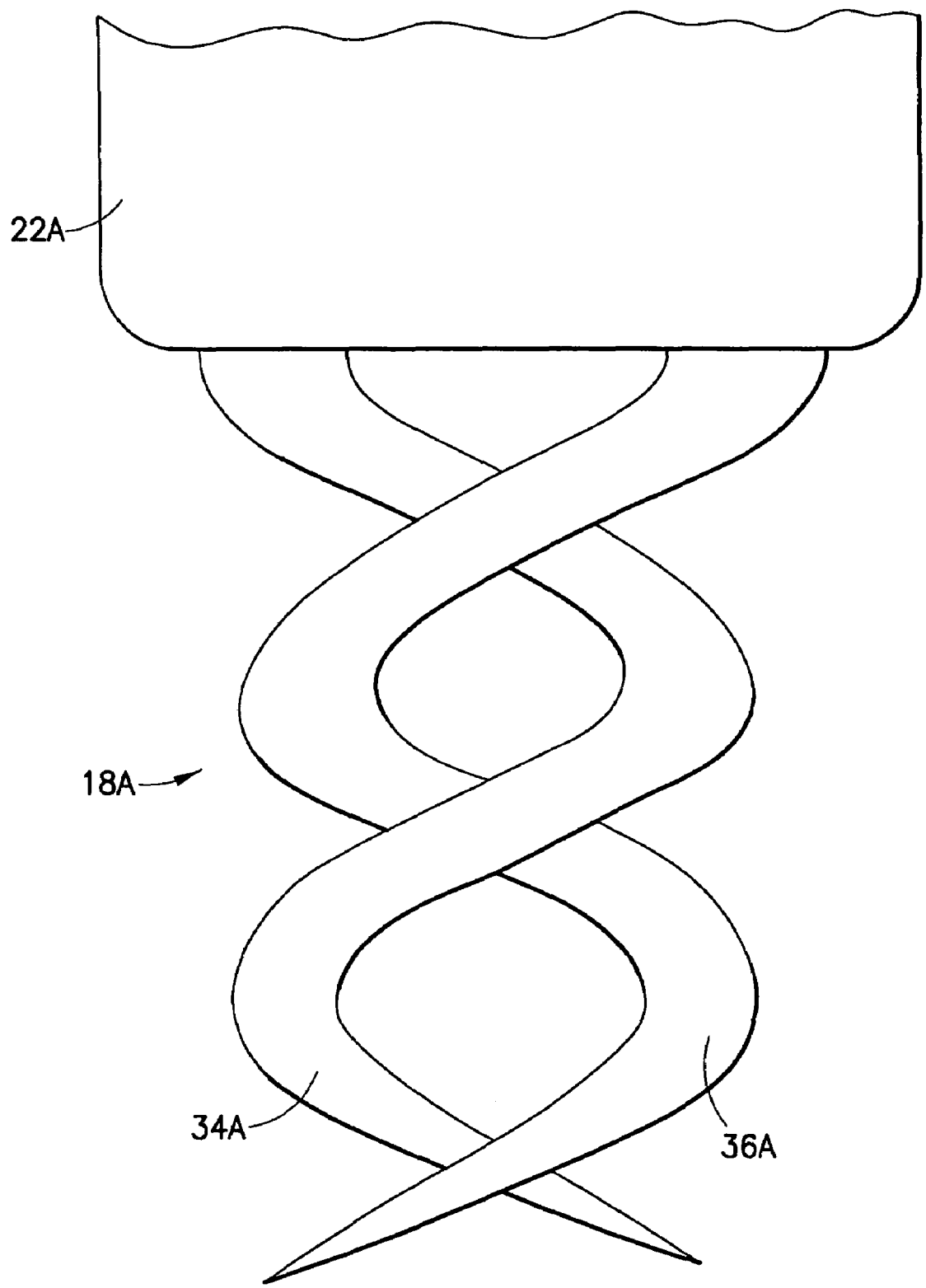
FIG. 4A is a detail elevation view of a distal end of a modified lead and specifically illustrating an electrode assembly which has no insulation on either of the helices.

FIG. 4A illustrates another embodiment of the invention in which a distal end 22A of a modified electrode assembly 18A including first and second active fixation helices 34A, 36A is totally free of insulation on their outer peripheral surfaces. In this instance, helix 34A is an anode and helix 36A is a cathode.

Figure 4B:
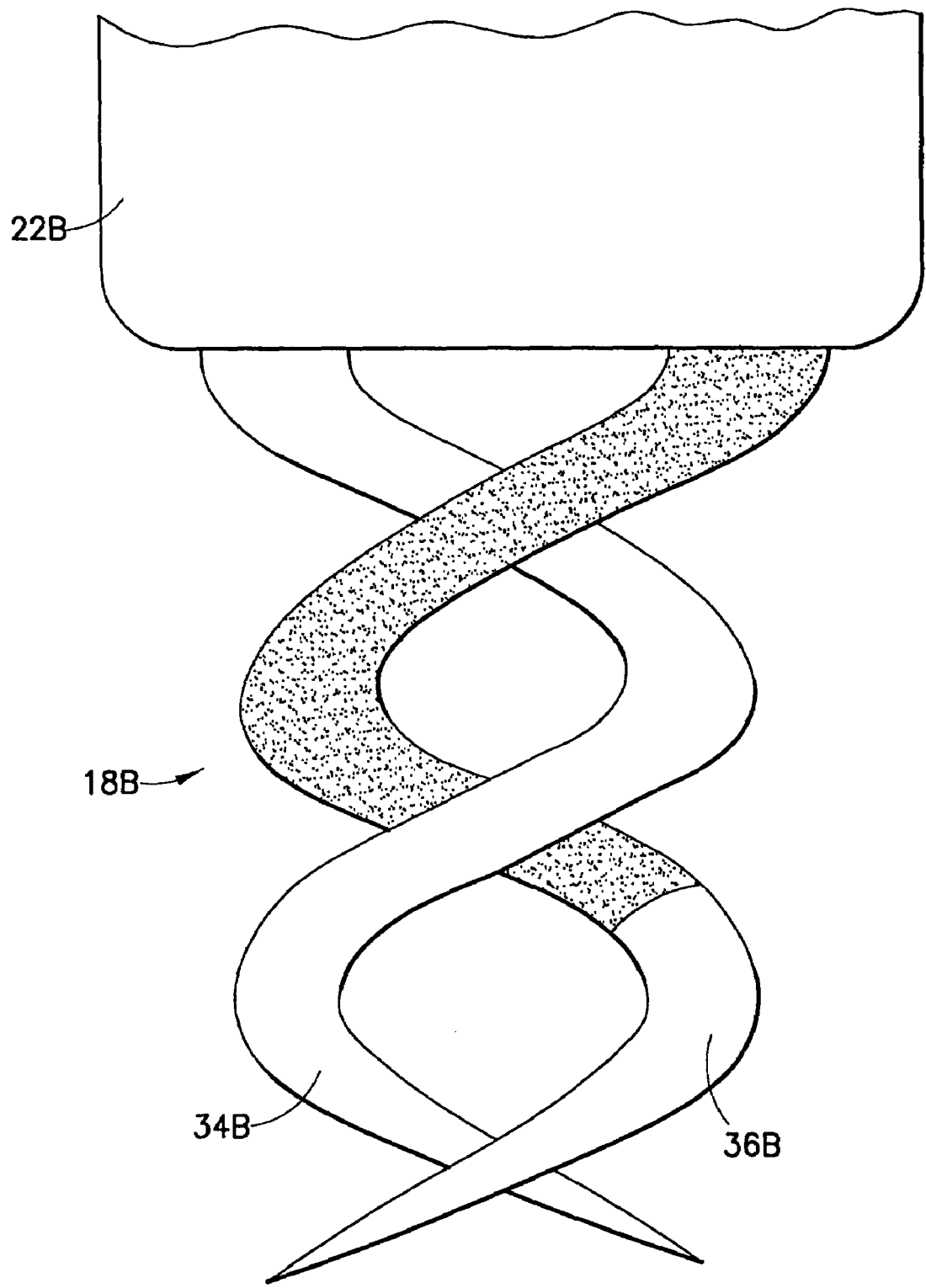
FIG. 4B is a detail elevation view of a distal end of another modified lead and specifically illustrating an electrode assembly which has insulation only on a portion of the anode electrode helix.

In another instance illustrated in FIG. 4B, a distal end 22B of a modified electrode assembly 18B includes a first active fixation helix 34B totally free of insulation on its outer peripheral surface while a second active fixation helix 36B is insulated on at least a portion of its outer peripheral surface. In this instance, helix 34B is an anode and helix 36B is a cathode.

Figure 5:
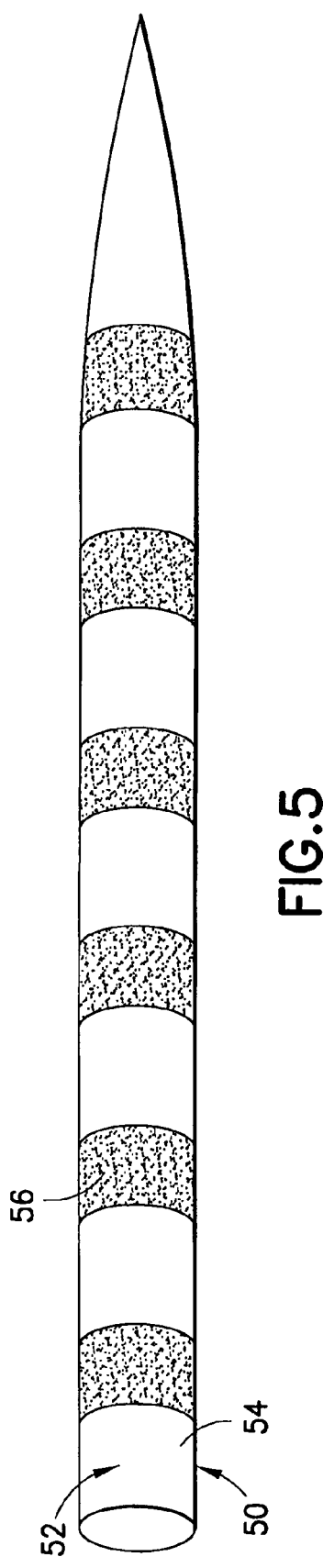
FIG. 5 is a detail perspective view of another embodiment in the form of an electrode configured as straight wire before being formed to the helix configuration.

While the FIG. 4 construction is desirable, a more favorable construction would be one in which the surface area of the cathode, at least, would be reduced to about three or four mm$^2$ so as to be adequate to assure that pacing impedance would be at least about 500 to 600 ohms. Thus, in one pre-helix formation illustrated in FIG. 5, that is, while an electrode 50 is configured as straight wire before being formed to the helix configuration of FIG. 4, about half of its outer peripheral surface 52 is insulated and about half of the outer peripheral surface is un-insulated. In this instance, the noninsulated portions 54 of the outer peripheral surface 52 coated with an insulative material are formed as a plurality of electrically active rings spaced by a plurality of electrically insulated rings 56, perhaps ceramic, titanium nitride (TiN) being a most suitable material for purposes of the invention. The insulative coatings may be sputter deposited ceramic material or applied by masking the outer peripheral surface 52 with fine, painted-on polymer, or by the application of ceramic material which is burned on or fused onto the outer peripheral surface 52.

Figure 6:
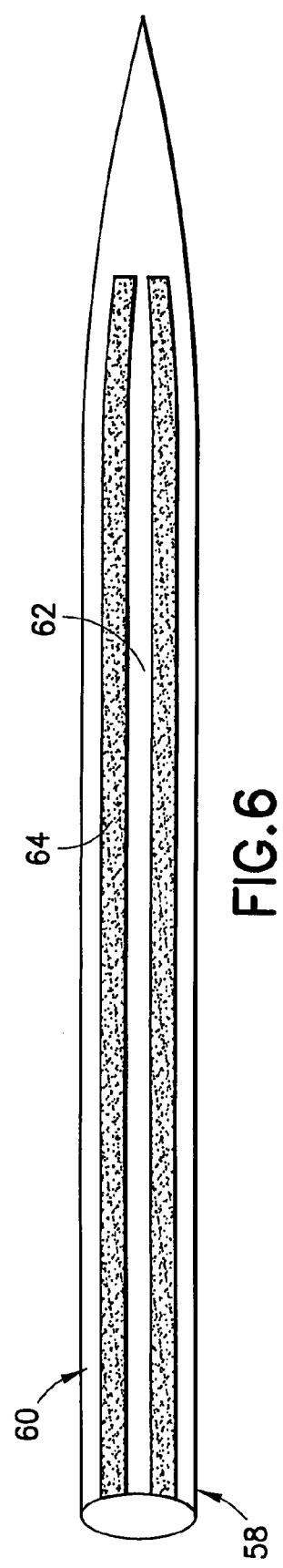
FIG. 6 is a detail perspective view of still another embodiment in the form of an electrode configured as straight wire before being formed to the helix configuration.

In another pre-helix formation illustrated in FIG. 6, an electrode 58 has an outer peripheral surface 60, again with alternating insulated and un-insulated portions, but in this instance, they are formed as a plurality of electrically active, or un-insulated, longitudinally extending strips 62 spaced by a plurality of electrically insulated longitudinally extending strips 64, again coated with a suitable insulative material.

Figure 7:
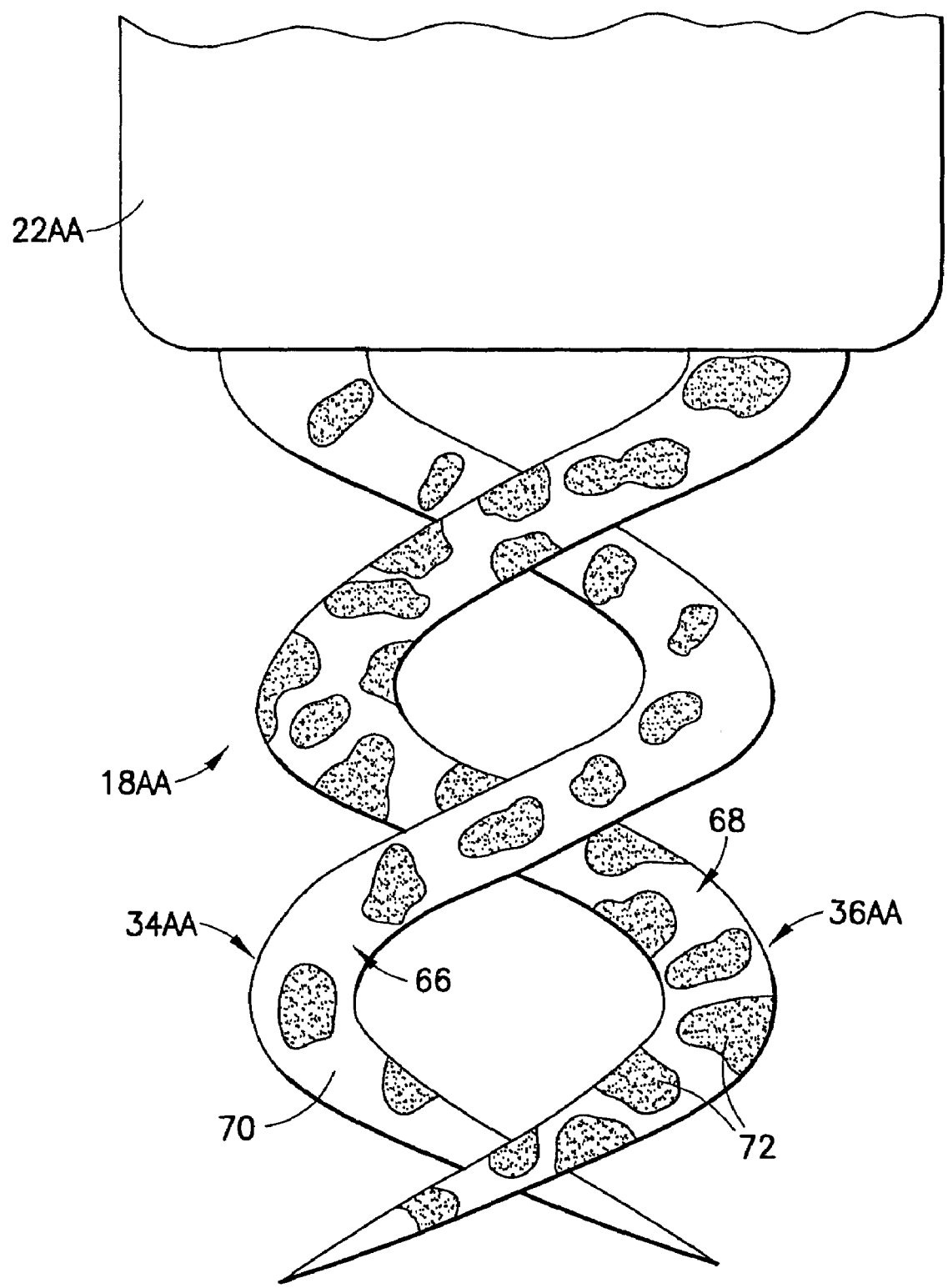
FIG. 7 is a detail elevation view of a distal end of a lead and specifically illustrating another electrode assembly.

Another embodiment of the invention may be seen at FIG. 7. In this instance, a modified electrode assembly 18AA includes first and second active fixation helices 34AA, 36AA, each having an outer peripheral surface 66, 68, respectively, with alternating insulated portions 70 and un-insulated portions 72. The un-insulated portions 72 are formed as a plurality of islands in a sea of the insulated portions 70 of the outer peripheral surfaces 66, 68 coated with a suitable insulative material.

Figure 8:
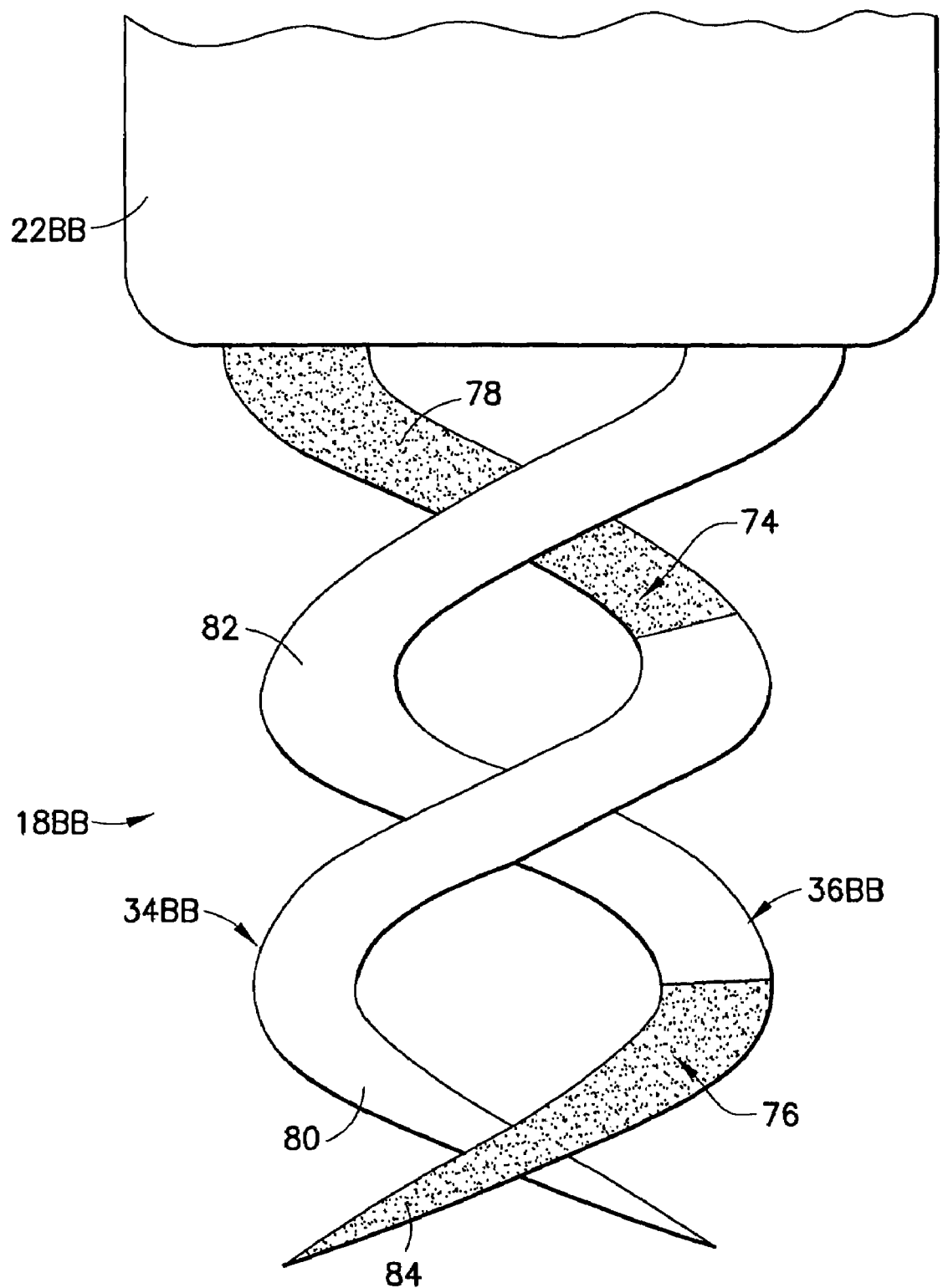
FIG. 8 is a detail elevation view of a distal end of a lead and specifically illustrating still another electrode assembly.

Still another embodiment of the invention may be seen at FIG. 8. In this instance, a modified electrode assembly 18BB includes first and second active fixation helices 34BB, 36BB, each having an outer peripheral surface 74, 76, respectively, with alternating insulated portions 78 and un-insulated portions 80. The first active fixation helix 34BB has a proximal portion 78 of its outer peripheral surface insulated and a distal portion 80 of its outer peripheral surface un-insulated. The second active fixation helix 36BB has a proximal portion 82 of its outer peripheral surface un-insulated and a distal portion 84 of its outer peripheral surface insulated.

Figure 9:
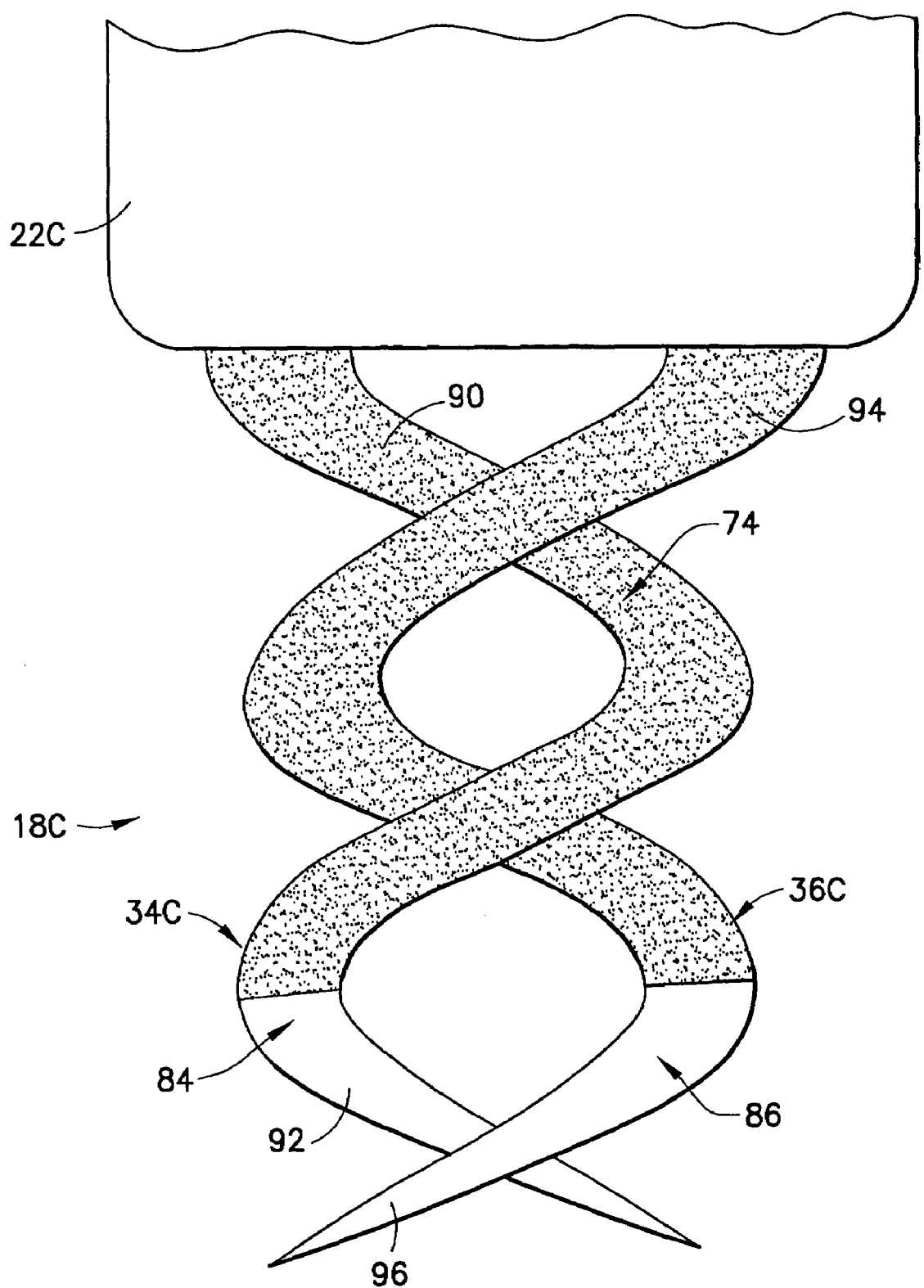
FIG. 9 is a detail elevation view of a distal end of a lead and specifically illustrating yet another electrode assembly.

Yet another embodiment of the invention may be seen at FIG. 9. In this instance, a modified electrode assembly 18C includes first and second active fixation helices 34C, 36C, each having an outer peripheral surface 86, 88, respectively. The first active fixation helix 34C has a proximal portion 90 of its outer peripheral surface insulated and a distal portion 92 of its outer peripheral surface un-insulated. Similarly, the second active fixation helix 36C has a proximal portion 94 of its outer peripheral surface insulated and a distal portion 96 of its outer peripheral surface un-insulated.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An implantable lead for use with an implantable medical device, comprising:

a lead body extending between a proximal end and a distal end;

first and second electrical conductors insulated from each other and extending from the proximal end to the distal end of the lead body;

an electrical connector coupled to the proximal end of the lead body;

first and second terminals electrically connected to respective ones of the first and second conductors; and an electrode assembly including first and second active fixation helices coupled to the distal end of the lead body, the first active fixation helix being an anode, the second active fixation helix being a cathode, the anode and the cathode being physically and electrically separated from each other;

wherein the first and second electrical conductors electrically interconnect each of the active fixation electrodes and the first and second terminals;

wherein each of the first and second active fixation helices has an outer peripheral surface with alternating insulated and un-insulated portions; and wherein the un-insulated portions of the outer peripheral surface of each of the first and second active fixation helices are formed as a plurality of islands in the insulated portions of the outer peripheral surfaces coated with an insulative ceramic material.

2. The implantable lead as set forth in claim 1 wherein the first and second active fixation helices are coaxial.

3. The implantable lead as set forth in claim 1
wherein each of the first and second active fixation helices has an outer peripheral surface with about half of the outer peripheral surface being insulated and about half of the outer peripheral surface being un-insulated.

4. The implantable lead as set forth in claim 1
wherein the first active fixation helix has a proximal portion of its outer peripheral surface insulated and a distal portion of its outer peripheral surface un-insulated; and wherein the second active fixation helix has a proximal portion of its outer peripheral surface un-insulated and a distal portion of its outer peripheral surface insulated.

5. The implantable lead as set forth in claim 1 wherein each of the first and second active fixation helices has a proximal portion of its outer peripheral surface insulated and a distal portion of its outer peripheral surface un-insulated.

6. The implantable lead as set forth in claim 1 wherein the lead body comprises an exterior surface having a single insulating sheath extending from the proximal end to the distal end of the lead body, and wherein the first and second electrical conductors are disposed within the single insulating.

7. The implantable lead as set forth in claim 1 wherein the distal end of the lead body is a single distal end such that the electrode assembly is disposed at the single distal end.

8. An implantable lead for use with an implantable medical device, comprising:
    a lead body extending between a proximal end and a distal end;
    first and second electrical conductors insulated from each other and extending from the proximal end to the distal end of the lead body;
    an electrical connector coupled to the proximal end of the lead body;
    first and second terminals electrically connected to respective ones of the first and second conductors; and
    an electrode assembly including first and second active fixation helices coupled to the distal end of the lead body, the first active fixation helix being an anode, the second active fixation helix being a cathode, the anode and the cathode being physically and electrically separated from each other;
    wherein the first and second electrical conductors electrically interconnect each of the active fixation electrodes and the first and second terminals;
    wherein each of the first and second active fixation helices has an outer peripheral surface with alternating insulated and un-insulated portions; and
    wherein the un-insulated portions of the outer peripheral surface of each of the first and second active fixation helices are formed as a plurality of islands in the insulated portions of the outer peripheral surfaces coated with an insulative polymeric material.

9. The implantable lead as set forth in claim 8 wherein the first and second active fixation helices are coaxial.

10. The implantable lead as set forth in claim 8 wherein the lead body comprises an exterior surface having a single insulating sheath extending from the proximal end to the distal end of the lead body, and wherein the first and second electrical conductors are disposed within the single insulating.

11. The implantable lead as set forth in claim 8 wherein the distal end of the lead body is a single distal end such that the electrode assembly is disposed at the single distal end.

12. An implantable lead for use with an implantable medical device, comprising:
    a lead body extending between a proximal end and a distal end;
    first and second electrical conductors insulated from each other and extending from the proximal end to the distal end of the lead body;
    an electrical connector coupled to the proximal end of the lead body;
    first and second terminals electrically connected to respective ones of the first and second conductors; and
    an electrode assembly including first and second active fixation helices coupled to the distal end of the lead body, the first active fixation helix being an anode, the second active fixation helix being a cathode, the anode and the cathode being physically and electrically separated from each other;
    wherein the first and second electrical conductors electrically interconnect each of the active fixation electrodes and the first and second terminals;
    wherein each of the first and second active fixation helices has an outer peripheral surface with alternating insulated and un-insulated portions; and
    wherein the un-insulated portions of the outer peripheral surface of each of the first and second active fixation helices are formed as a plurality of electrically active rings spaced by a plurality of electrically insulated rings coated with an insulative ceramic material.

13. The implantable lead as set forth in claim 12 wherein the first and second active fixation helices are coaxial.

14. The implantable lead as set forth in claim 12 wherein the lead body comprises an exterior surface having a single insulating sheath extending from the proximal end to the distal end of the lead body, and wherein the first and second electrical conductors are disposed within the single insulating.

15. The implantable lead as set forth in claim 12 wherein the distal end of the lead body is a single distal end such that the electrode assembly is disposed at the single distal end.

16. An implantable lead for use with an implantable medical device, comprising:
    a lead body extending between a proximal end and a distal end;
    first and second electrical conductors insulated from each other and extending from the proximal end to the distal end of the lead body;
    an electrical connector coupled to the proximal end of the lead body;
    first and second terminals electrically connected to respective ones of the first and second conductors; and
    an electrode assembly including first and second active fixation helices coupled to the distal end of the lead body, the first active fixation helix being an anode, the second active fixation helix being a cathode, the anode and the cathode being physically and electrically separated from each other;
    wherein the first and second electrical conductors electrically interconnect each of the active fixation electrodes and the first and second terminals;
    wherein each of the first and second active fixation helices has an outer peripheral surface with alternating insulated and un-insulated portions; and
    wherein the un-insulated portions of the outer peripheral surface of each of the first and second active fixation helices are formed as a plurality of electrically active rings spaced by a plurality of electrically insulated rings coated with an insulative polymeric material.

17. The implantable lead as set forth in claim 16 wherein the first and second active fixation helices are coaxial.

18. The implantable lead as set forth in claim 16
wherein the lead body comprises an exterior surface having a single insulating sheath extending from the proximal end to the distal end of the lead body, and wherein the first and second electrical conductors are disposed within the single insulating.

19. The implantable lead as set forth in claim 16 wherein the distal end of the lead body is a single distal end such that the electrode assembly is disposed at the single distal end.

20. An implantable lead for use with an implantable medical device, comprising:
   a lead body extending between a proximal end and a distal end;
   first and second electrical conductors insulated from each other and extending from the proximal end to the distal end of the lead body;
   an electrical connector coupled to the proximal end of the lead body;
   first and second terminals electrically connected to respective ones of the first and second conductors; and
   an electrode assembly including first and second active fixation helices coupled to the distal end of the lead body, the first active fixation helix being an anode, the second active fixation helix being a cathode, the anode and the cathode being physically and electrically separated from each other;
   wherein the first and second electrical conductors electrically interconnect each of the active fixation electrodes and the first and second terminals;
   wherein each of the first and second active fixation helices has an outer peripheral surface with alternating insulated and un-insulated portions; and
   wherein the un-insulated portions of the outer peripheral surface of each of the first and second active fixation helices are formed as a plurality of electrically active longitudinally extending strips spaced by a plurality of electrically insulated longitudinally extending strips coated with an insulative ceramic material.

21. The implantable lead as set forth in claim 20
wherein the first and second active fixation helices are coaxial.

22. The implantable lead as set forth in claim 20
wherein the lead body comprises an exterior surface having a single insulating sheath extending from the proximal end to the distal end of the lead body, and wherein the first and second electrical conductors are disposed within the single insulating.

23. The implantable lead as set forth in claim 20
wherein the distal end of the lead body is a single distal end such that the electrode assembly is disposed at the single distal end.

24. An implantable lead for use with an implantable medical device, comprising:
   a lead body extending between a proximal end and a distal end;
   first and second electrical conductors insulated from each other and extending from the proximal end to the distal end of the lead body;
   an electrical connector coupled to the proximal end of the lead body;
   first and second terminals electrically connected to respective ones of the first and second conductors; and
   an electrode assembly including first and second active fixation helices coupled to the distal end of the lead body, the first active fixation helix being an anode, the second active fixation helix being a cathode, the anode and the cathode being physically and electrically separated from each other;
   wherein the first and second electrical conductors electrically interconnect each of the active fixation electrodes and the first and second terminals;
   wherein each of the first and second active fixation helices has an outer peripheral surface with alternating insulated and un-insulated portions; and
   wherein the un-insulated portions of the outer peripheral surface of each of the first and second active fixation helices are formed as a plurality of electrically active longitudinally extending strips spaced by a plurality of electrically insulated longitudinally extending strips coated with an insulative polymeric material.

25. The implantable lead as set forth in claim 24
wherein the first and second active fixation helices are coaxial.

26. The implantable lead as set forth in claim 24
wherein the lead body comprises an exterior surface having a single insulating sheath extending from the proximal end to the distal end of the lead body, and wherein the first and second electrical conductors are disposed within the single insulating.

27. The implantable lead as set forth in claim 24
wherein the distal end of the lead body is a single distal end such that the electrode assembly is disposed at the single distal end.

* * * * *